US010939838B2

(12) United States Patent
Similowski et al.

(10) Patent No.: US 10,939,838 B2
(45) Date of Patent: Mar. 9, 2021

(54) METHOD FOR CHARACTERIZING THE PHYSIOLOGICAL STATE OF A PATIENT FROM THE ANALYSIS OF THE CEREBRAL ELECTRICAL ACTIVITY OF SAID PATIENT, AND MONITORING DEVICE APPLYING SAID METHOD

(71) Applicants: UNIVERSITE PIERRE ET MARIE CURIE (PARIS 6), Paris (FR); CENTRE NATIONAL DE LA RECHERCHE SCIENTIFIQUE, Paris (FR); FONDATION ICM—INSTITUT DU CERVEAU ET DE LA MOELLE EPINIERE, Paris (FR); INSTITUT NATIONAL DE LA SANTE ET DE LA RECHERCHE MEDICALE, Paris (FR); ASSISTANCE PUBLIQUE—HOPITAUX DE PARIS, Paris (FR)

(72) Inventors: Thomas Similowski, Issy-les-Moulineaux (FR); Mathieu Raux, Paris (FR); Mario Chavez, Choisy le Roi (FR); Jacques Martinerie, Palaiseau (FR); Pierre Pouget, Paris (FR)

(73) Assignees: UNIVERSITE PIERRE ET MARIE CURIE (PARIS 6), Paris (FR); CENTRE NATIONAL DE LA RECHERCHE SCIENTIFIQUE, Paris (FR); FONDATION ICM—INSTITUT DU CERVEAU ET DE LA MOELLE EPINIERE, Paris (FR); INSTITUT NATIONAL DE LA SANTE ET DE LA RECHERCHE MEDICALE, Paris (FR); ASSISTANCE PUBLIQUE—HOPITAUX DE PARIS, Paris (FR)

( * ) Notice: Subject to any disclaimer, the term of this patent is extended or adjusted under 35 U.S.C. 154(b) by 521 days.

(21) Appl. No.: 14/398,217
(22) PCT Filed: May 3, 2013
(86) PCT No.: PCT/EP2013/059279
§ 371 (c)(1),
(2) Date: Oct. 31, 2014
(87) PCT Pub. No.: WO2013/164462
PCT Pub. Date: Nov. 7, 2013

(65) Prior Publication Data
US 2015/0119745 A1 Apr. 30, 2015

(30) Foreign Application Priority Data
May 3, 2012 (FR) .................................. 12 54089

(51) Int. Cl.
A61B 5/04 (2006.01)
A61B 5/048 (2006.01)
(Continued)

(52) U.S. Cl.
CPC ........ A61B 5/04015 (2013.01); A61B 5/0036 (2018.08); A61B 5/048 (2013.01);
(Continued)

(58) Field of Classification Search
CPC ........ A61M 2230/10; A61M 2230/005; A61B 5/048; A61B 5/04015
See application file for complete search history.

(56) References Cited

U.S. PATENT DOCUMENTS

2004/0254493 A1   12/2004   Chervin et al.
2007/0208269 A1    9/2007   Mumford et al.

FOREIGN PATENT DOCUMENTS

FR   2 903 314 A1   1/2008
FR   2 962 322 A1   1/2012
(Continued)

OTHER PUBLICATIONS

Koles, Zoltan J., Michael S. Lazar, and Steven Z. Zhou. "Spatial patterns underlying population differences in the background EEG." Brain topography 2.4 (1990): 275-284.*
International Search Report of PCT/EP2013/059279 dated Jul. 31, 2013 [PCT/ISA/210].

Primary Examiner — Jacqueline Cheng
Assistant Examiner — Michael A Catina
(74) Attorney, Agent, or Firm — Sughrue Mion, PLLC

(57) ABSTRACT

The invention relates to a method for detecting a physiological state of a patient deviating from a reference physiologi-
(Continued)

cal state, in which, after having determined, in each of Q frequency bands, R reference matrices $PR_{q,r}$ with qe[1 . . . Q] and re[1 . . . R] which correspond to the reference physiological state, the following steps are repeated in a loop: carrying out measurements, in M time segments, of an electroencephalographic signal; filtering and centering the measurements in Q frequency bands to obtain and determine M×Q scaled matrices of spatial covariance; for each time segment m, calculating a deviation from the reference physiological state, and comparing each of the deviations from the reference physiological state to a predefined threshold. The invention also relates to a monitoring device applying said method.

20 Claims, 2 Drawing Sheets

(51) Int. Cl.
    *A61B 5/00*     (2006.01)
    *A61M 16/00*     (2006.01)

(52) U.S. Cl.
    CPC ....... *A61B 5/4836* (2013.01); *A61M 16/0051* (2013.01); *A61M 2209/082* (2013.01); *A61M 2230/10* (2013.01)

(56) References Cited

FOREIGN PATENT DOCUMENTS

| | | |
|---|---|---|
| WO | 97/16216 A1 | 5/1997 |
| WO | 2010/060153 A1 | 6/2010 |

* cited by examiner

METHOD FOR CHARACTERIZING THE PHYSIOLOGICAL STATE OF A PATIENT FROM THE ANALYSIS OF THE CEREBRAL ELECTRICAL ACTIVITY OF SAID PATIENT, AND MONITORING DEVICE APPLYING SAID METHOD

CROSS REFERENCE TO RELATED APPLICATIONS

This application is a National Stage of International Application No. PCT/EP2013/059279, filed May 3, 2013, claiming priority based on French Patent Application No. 12 54089, filed May 3, 2012, the contents of all of which are incorporated herein by reference in their entirety.

The invention relates to a method for characterizing the physiological state of a patient from the analysis of his or her cerebral electrical activity. The invention also relates to a monitoring device applying said method.

Although having been more particularly developed as part of a research program relating to a study of the discords that can occur between a patient and the breathing assistance device to which the patient is connected, the method of the invention has a scope ranging far beyond that particular application.

In effect, since the method of the invention allows for the characterization of physiological states and therefore the detection of a physiological state deviating from a reference physiological state, it can therefore in particular be used to detect specific cognitive periods of certain psychophysiological states (levels of vigilance, visual recognition) or emotional states (fear, joy, etc.) or even to detect pathological periods, such as, for example, a pending epileptic seizure, and, if necessary, provide a warning signal necessary to allow for a prevention or therapeutic intervention. The method of the invention can also be used, in sleep, to differentiate the different sleep states, or, in anesthesia, to characterize sleep states under anesthesia with possibly an automatic control of the regulation of the substance injected.

BACKGROUND OF THE INVENTION

Mechanical breathing assistance constitutes a vital relief measure whose prime aim is to mitigate the acute or chronic failures of the respiratory system, such as, for example, in a case of severe pneumonia. It consists in supplying a predetermined volume of gas or in pressurizing the airways, by means of an interface (mask, intubation tube or tracheotomy canula). In both cases, various adjustments make it possible to adapt the flow of gas to the needs of the patient.

This is a therapeutic approach which is very frequently used in the operating block, in resuscitation, in the post-intervention monitoring room, in emergencies even in the ambulances of the French Ambulance and Emergency Unit (SMUR), or even in the home, in cases of respiratory failure. It relates to approximately one in every two patients admitted for resuscitation in France and to an incidence of 2.7 per thousand inhabitants in the United States, or approximately 250 000 patients per year in 2000 and a projected 650 000 patients per year in 2020. A third of these patients are ventilated for more than four days.

In addition to its physiological respiratory assistance effects, the mechanical ventilation relieves the dominant symptom of the respiratory failure that is dyspnea. It thus has to fulfill the dual function of improving the oxygenation and purging carbon dioxide, and ensuring the comfort of the patient. Failing this, like any ill-suited therapy, it can become damaging and even responsible for iatrogenic complications. It is therefore of prime importance that the aid delivered by the mechanical ventilation is perfectly matched to the needs of the patient. The latter must be in harmony with the ventilator which delivers the mechanical ventilation.

The modalities of monitoring the physiological effects of the respiratory assistance are well codified and simple to use (measurements of physical quantities whose values appear on the screen of the ventilator), but the modalities for assessing the patient/ventilator harmony, considered from a sensory angle, are few, little codified, and little used. This is particularly true among the barely communicative patients, commonplace in resuscitation. The issue is to detect the situations during which the patient and ventilator are no longer in harmony. This is referred to as discord.

This discord is not only uncomfortable for the patient, it appears damaging to his or her future. In effect, the delivery of breathing assistance inappropriate to the needs of the patient is associated with an increase in the duration of the mechanical ventilation and the stay in resuscitation, as well as with psychological problems of post traumatic stress disorder type.

Daily experience shows that the research into a discord by means of clinical examination is difficult and little practiced. It in effect demands that both the patient and his or her ventilator be monitored. In effect, the detection of this type of episode relies partly on the analysis of the plots of pressure and of flow rate in the airways supplied by the ventilator. The multiplicity of the events, which, in addition, can coexist simultaneously, makes searching for them all the more tedious when the carer cannot be constantly at the patient's bedside.

Also, although present in approximately one patient in every two receiving breathing assistance while conscious, the breathing discomfort, or dyspnea, is only very rarely looked into during the examination of the patient under mechanical ventilation. Verbal expression is difficult. Non-verbal expression (analysis of facial mimics) is probably useful but its clinical value is not documented.

Thus, the clinical diagnostic tools are not efficient in detecting a discord between a patient and his or her ventilator. Nor can they be considered among patients ventilated in the home because of a chronic pathology (20% of ventilated patients are outside of a care structure), failing the constant presence of a carer on site. In light of the severity of the complications associated with a patient/ventilator discord, it appears necessary to have tools that make it possible to detect such a situation, in order to alert the carers in order for them to remedy them.

Two of the inventors have developed discord detection systems based on the analysis of the electro-encephalographic signal linked to the ventilation (cerebral electrical activity collected by means of surface electrodes).

Thus, the document FR-A-2 903 314 describes a device and a method for detecting a discord between a patient and a breathing assistance machine consisting, for each breathing cycle, in measuring an electro-encephalographic signal over a measurement interval extending around the start of inhalation, then in averaging the electro-encephalographic signals measured over several measurement intervals and finally processing the duly obtained averaged signal to deduce therefrom any discord between the patient and the breathing assistance machine. Such a method does not give full satisfaction. In effect, the situations of breathing discomfort or distress are frequently associated with movements of the patient causing spurious electrical activity in the electroencephalogram making it difficult to interpret. Also, the detection method described in this document entails measuring and averaging an electro-encephalographic signal over at least 60 to 80 breathing cycles to be able to conclude on the existence of a discord. Now, 60 to 80 breathing cycles correspond, on average, to four to five minutes, during which, if a discord exists, the patient is in distress. In the situations of breathing discomfort or distress resulting from a discord between the patient and the ventilator, it is important to be able to detect this discord and remedy it as rapidly as possible to restore the harmony between the patient and his or her ventilator.

In order to neutralize the problem of the contamination of the electro-encephalographic signal linked to the ventilation and allow for it to be processed more rapidly, the document FR-A-2 962 322 again describes electroencephalogram analysis device and method. The method consists in collecting the electroencephalogram through multiple electrodes placed on the scalp of the patient. The signal collected is then filtered in a frequency band lying between 0.03 and 40 Hz, and its power is computed. The comparison of the power of the signal preceding inhalation to that of a reference period makes it possible to highlight an episode of discord when the system objectifies a reduction of power. However, the method described in this document does not however give full satisfaction. In effect, it allows for the analysis only of the inhalation part of the ventilation, excluding the exhalation phase, even though the latter can be the source of discord. Moreover, it requires a simultaneous recording of the ventilation in order to synchronize the analysis of the electroencephalogram.

OBJECT OF THE INVENTION

One aim of the invention is to propose a method for characterizing the physiological state of a patient from the analysis of his or her cerebral activity and a device applying said method, in order to detect specific states of such or such a situation of the patient, and in particular a situation of discord with the medical assistance device to which the patient is connected.

SUMMARY OF THE INVENTION

In order to achieve this aim, a method is proposed for detecting a physiological state of a patient deviating from a reference physiological state, in which, after having determined, in each of Q frequency bands, a reference pole $PR_q$ with $q \in [1 \ldots Q]$ corresponding to the reference physiological state, the following steps are repeated in a loop:
performing measurements, in M time segments, of an electro-encephalographic signal of the patient along n pathways and at p instants to generate M measurement matrices $X_m$ containing n×p samples, for $m \in [1 \ldots M]$;
filtering and centering each measurement matrix Xm in the Q frequency bands to obtain M×Q filtered measurement matrices $X_{m,q}$ and determining M×Q standardized matrices of spatial covariance $C_{m,q}$ by the formula $C_{m,q} = (X_{m,q} X_{m,q}^T)/\text{trace}(X_{m,q} X_{m,q}^T)$;
for each time segment m, determining distances $d_{m,q}$ between each standardized matrix of spatial covariance $C_{m,q}$ and the reference pole $PR_q$, and determining a deviation $e_m$ from the reference physiological state as a function of the distances $d_{m,q}$;
comparing each of the deviations $e_m$ from the reference physiological state to a determined threshold S.

If the threshold S is exceeded by one of the deviations, the physiological state of the patient is then declared deviant relative to the reference physiological state.

The reference poles $PR_q$ can be determined in a number of ways. According to a first implementation, the reference poles $PR_q$ are made up of prototypes or reference matrices $PR_{q,r}$ determined according to the following steps:
performing measurements, in M time segments, of an electro-encephalographic signal of the patient along n pathways and at p instants to generate M measurement matrices $X_m^{ref}$ of size n×p for $m \in [1 \ldots M]$, while the patient is in the reference physiological state;
filtering and centering each measurement matrix Xm in the Q frequency bands to obtain M×Q filtered measurement matrices $X_{m,q}^{ref}$ and determining M×Q standardized matrices of spatial covariance by the formula $C_{m,q}^{ref} = (X_{m,q}^{ref} X_{m,q}^{ref\,T})/\text{trace}(X_{m,q}^{ref} X_{m,q}^{ref\,T})$;
determining, in each frequency band, R prototypes $PR_{q,r}$ $r \in [1 \ldots R]$ from the standardized matrices of spatial covariance $C_{m,q}^{ref}$ by using the dynamic swarms algorithm.

Thus, the reference pole $PR_q$ of each frequency band consists of all the prototypes $PR_q$, $r \in [1 \ldots R]$ of the corresponding frequency band. The distances $d_{m,q}$ of each standardized matrix of spatial covariance $C_{m,q}$ to the reference pole are then given by $$d_{m,q} = \arg\left\{\min_{r=1\ldots R} dist(C_{m,q}, PR_{q,r})\right\},$$

and the deviation from the reference situation is given by $$e_m = \sum_{q=1}^{Q} d_{m,q}$$

The threshold S is preferably determined according to the following steps:
computing distances $d_{m,q}^{ref}$ between each covariance matrix $C_{m,q}^{ref}$ and the prototype of the prototypes $PR_{q,r}$ which is the closest thereto;
determining the median distance DM of all these duly computed distances $d_{m,q}^{ref}$, the threshold S being determined from the arithmetic mean MVA of the absolute values of the deviations of each of the distances $d_{m,q}^{ref}$ from the median distance DM.

According to another implementation, the reference pole $PR_q$ of each frequency band is made up of the projection on the main geodesic curves defined by the covariance matrices $C_{m,q}^{ref}$ which maximizes the quantity of information (for example to at least 95%). This technique is an extension of the main components analysis in the case of vector spaces (see Fletcher (2004)).

The distances $d_{m,q}$ between each standardized matrix of spatial covariance $C_{m,q}$ to the corresponding reference pole are then given by the projection of each of the standardized matrices of spatial covariance $C_{m,q}$ on the corresponding main geodesic curves. The deviation from the reference situation is given by $$e_= = \sum_{q=1}^{Q} d_{m,q}$$

Preferably, the distance between the matrices used in the method of the invention is the following Riemannian distance:

$$dist(P_1, P_2) = \left\{ \sum_{k=1}^{K} \ln^2(\lambda_k) \right\}^{1/2}$$

in which the $\lambda_k$ are the K specific values of the joint matrix $P_1^{-1} \cdot P_2$.

Thus, contrary to the conventional methods in which the electro-encephalographic measurements are exploited either by the study of the potentials mentioned linked to a time reference (the throughput signal in this case, as in FR-A-2 903 314), or by the analysis of the frequency spectrum (as in FR-A-2 962 322), the method of the invention prioritizes the study of the temporal relationships between the phase components of the different electro-encephalographic signals. The use of the synchronies method makes it possible to describe the space-time distribution of the active neural sources during the electro-encephalographic recording, and therefore constitutes a novel approach to the interactions and the characterization of the neural network.

The invention also relates to a device for monitoring a patient to detect a physiological state deviating from a reference state of the patient, the monitoring device comprising measurement means for measuring the electro-encephalographic signals of the patient, real-time signal processing means for implementing the method of the invention from the duly measured signals, and reaction means for reacting to a threshold overshoot.

According to a first variant, the reaction means comprise a warning device suitable for delivering a warning signal in response to the threshold overshoot.

According to a second variant, the reaction means comprise a setpoint generator intended for a medical assistance device to which the patient is connected, the setpoint generator being adapted to vary the setpoint in response to the threshold overshoot to modify the operation of the medical assistance device in such a way as to return the patient to the reference physiological state.

BRIEF DESCRIPTION OF THE DRAWINGS

The invention will be better understood in light of the following description of a particular implementation, with reference to the figures of the attached drawings, in which.

DETAILED DESCRIPTION OF THE INVENTION

Figure 1:
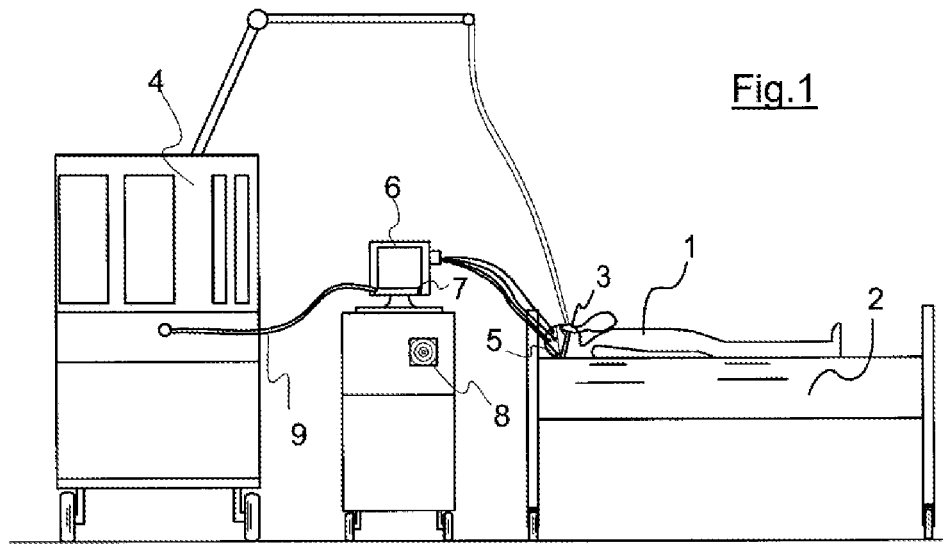
FIG. 1 is a schematic view of a medicalized station with a bed receiving a patient, a breathing assistance device and a monitoring device according to the invention used to control the breathing assistance device.

The invention will now be detailed with reference to its application to the detection of discord between a patient and the breathing assistance device to which he or she is connected. It is assumed here that, in the event of discord, the cerebral activity of the patient is modified relative to a reference physiological state in which the patient is in harmony with the breathing assistance device.

Any cognitive act results from a cooperation between several spatially distributed neural networks (Varela et al., 2001). At the current time, and despite their recent advances, the main cerebral imaging techniques (electro-encephalography, magnetoencephalography, functional magnetic resonance imaging and position emission tomography) provide only a mapping of the cerebral activations, without directly taking into account interactions between these activations.

The invention is based on the assumption whereby the dynamic links between the neural groups are manifested by the synchronization of oscillatory activities in a frequency band (Varela et al., 2001). Numerous experimental results in animals obtained through recordings by microelectrodes already validate this assumption of synchrony. In humans, studies have shown the existence of synchronizations between remote regions, linked to the cognitive context (Rodriguez et al. 1999).

The assumption of a role of the synchronies in the integration of the cerebral activities was originally proposed by Milner in 1974 to resolve the problem of the figure/background segmentation in a visual scene. Milner proposed that the neurons responding to the figure discharge synchronously, whereas those coding for the background discharge randomly. This assumption was consequently taken up by Freeman (Freeman, 1975) and supported by works on the olfactory bulb of rabbits, and then by Von der Marlsburg (Von der Marlsburg, 1981) before sinking into relative oblivion. However, the discovery of synchronous oscillations in animals in the band γ (30-70 Hz) by Gray and Singer (Gray and Singer, 1989) in the visual cortex of cats re-excited interest in this idea: this study showed that two neurons of the visual cortex discharge in phase at frequencies in the vicinity of 40 Hz in response to stimulations which seem to originate from the same object. Conversely, if the stimuli do not seem to originate from the same object, the neurons discharge also, but not in synchrony.

These results fit into an approach which can be expressed in terms of resonant cell assemblies (Varela 1995; Damasio 1990; Llinas, Ribary et al. 1994): the emergence of any cognitive act would correspond to the transient selection of a distributed subset of neurons linked by strong reciprocal connections (a cell assembly). Because of its very dense network of interconnections, the brain contains an almost infinity of assemblies of this type and each neuron can belong, at different instants, to a myriad of assemblies. The selection would be made by rapidly placing the different neurons belonging to the assembly in synchrony in a specific frequency band (resonance). The synchrony would act as a "glue" enabling neurons to assemble temporarily in a resonant assembly, and thereby allowing for the neural integration necessary to a cognitive act.

It is useful to distinguish two levels of assemblies. At a local level, the formation of micro-assemblies in one and the same cortical area would allow the integration of information of the same kind (visual, audible). These local links would correspond to the synchronies observed in animals between close neurons (Singer 1995). These micro-assemblies could, in turn, enter into synchrony to form macro-assemblies linking remote cerebral areas. These macro-assemblies would allow for the integration of processes of different kinds in complex cognitive acts.

The aim of the present invention is to exploit these assumptions to recognize a change of the cerebral activity linked to an unusual situation, for example a situation of "modified" breathing (inhalatory stress, as can be simulated in the laboratory, or encountered in pathology or under mechanical breathing assistance), compared to a reference activity or physiological state. The recognition of such a situation makes it possible, for example, to order a modification of the operation of the breathing assistance device to return the patient to a situation of comfort characterized by a normal cerebral activity.

Having set the general context of the invention, the method of the invention will now be detailed. The principle of the invention is first explained with reference to FIG. 1, in which can be seen the patient 1 lying on a bed 2 and equipped with a mask 3 connected by an air intake to a breathing assistance device 4. The patient is equipped with a headset 5 bearing n electrodes designed to measure electro-encephalographic signals. The headset 5 is connected to a monitoring device 6, here a computer comprising a central unit 7 executing a monitoring program, which receives the electro-encephalographic measurements, processes them, and generates in response setpoints intended for the breathing assistance device to which the monitoring device 6 is connected.

Figure 2:
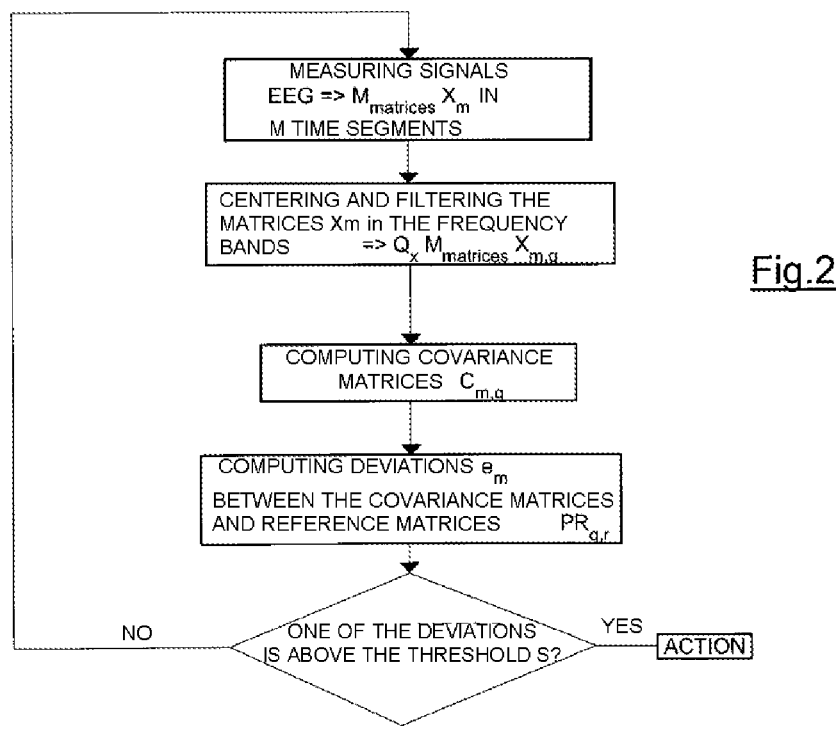
FIG. 2 is a flow diagram describing the implementation of the method of the invention by the monitoring device of FIG. 1.

The monitoring device implements a real-time monitoring algorithm, illustrated in FIG. 2, which implements the method of the invention to permanently monitor the electro-encephalographic activity of the patient. The advantage of the method of the invention is that the monitoring cycle is very short and the monitoring device can thus react rapidly to the detection of a deviant physiological state.

The device here comprises means for reacting to the detection of a threshold overshoot, for example a loudspeaker 8 for emitting an alarm, and thus warning the caring personnel, but is also programmed to generate a setpoint intended for the breathing assistance device 4 to which it is connected by a cable 9.

Figure 3:
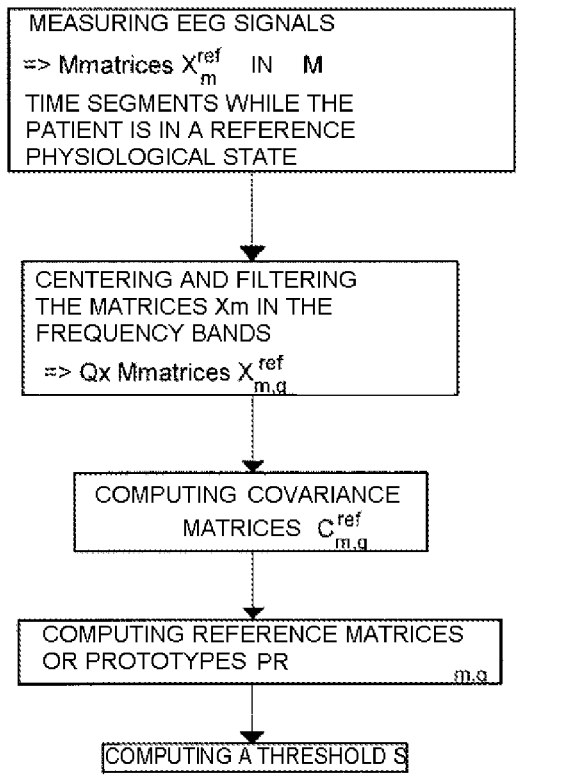
FIG. 3 is a flow diagram describing the preliminary step of determining the reference matrices and the threshold characterizing the reference physiological state.

To operate, the monitoring device 6 must have first characterized a reference physiological state of the patient, for example a state of comfort in which the patient feels no breathing discomfort. For this, as indicated in FIG. 3, the monitoring device 6 measures electro-encephalographic signals of the patient in real-time and thus performs the measurements in M time segments.

Each measurement gives rise to a matrix $X_m^{ref}$ of n signals measured at p instants during the time segment m, thus forming p samples in each time segment. Then, the monitoring device 6 filters and centers each measurement matrix $X_m^{ref}$ in Q frequency bands (preferably the five usual frequency bands for studying electro-encephalograms: 1-4 Hz, 4-8 Hz, 8-12 Hz, 12-24 Hz and 24-48 Hz) to obtain M×Q filtered reference measurement matrices $X_{m,q}^{ref}$.

From the filtered measurement matrices, the monitoring device 6 determines M×Q standardized reference matrices of spatial covariance $C_{m,q}^{ref}$ by the formula:

$$C_{m,q}^{ref} = (X_{m,q}^{ref} \cdot X_{m,q}^{ref\,T})/\text{trace}(X_{m,q}^{ref} \cdot X_{m,q}^{ref\,T}).$$

The spatial covariance matrices $C_{m,q}^{ref}$ characterize the synchronization of the neural activities over time. These spatial covariance matrices comprise, in the diagonal, the local synchronizations and, outside the diagonal, the remote synchronizations which are then the characteristics of the dynamics of the neural network.

Then, in each frequency band, reference matrices or prototypes $PR_{q,r}$, $r \in [1 \ldots R]$ are determined from the distribution of the spatial covariance matrices $C_{m,q}^{ref}$. Each prototype is a representative of a sub-class of the synchronization, and is here estimated by a Karcher means of the neighboring reference matrices of spatial covariance $C_{m,q}^{ref}$. The procedure for computing the prototypes $PR_{q,r}$ used in the present implementation is described hereinbelow and is applied for each frequency band. This computation here relies on the dynamic swarms algorithm (E. Diday, 1971) adapted to the Riemannian metric. It will in effect be noted that, in processing the signal the conventional Frobenius norm is usually used to define distances between covariance matrices (which are by definition positive-definite Hermitian matrices). This approach presupposes a normed vector space of zero curvature. However, the space of the positive-definite Hermitian matrices pertains rather to the metric spaces with negative curvature. The approach proposed in the context of the invention preferably uses the tools of Riemannian geometry to manipulate the covariance matrices. In this context, the distance between two matrices corresponds to the geodesic in the space generated by their Hermitian property; and the mean of the covariance matrices no longer corresponds to an arithmetic mean as conventionally, but to a geometrical mean.

1: procedure
    C is a table of M covariance matrices.
    L is the number of prototypes
2: k:=M
3: eps:=$10^{-8}$
4: kk:=random(k)
5: $PR^j:=C_{kk(j)}$; j:=1:L; $PR\_new^j:=0$
6: as long as abs ($PR\_new^j - PR^j$)>eps
7:   $PR\_new^j := PR^j$;
8:   for i:=1 to k
9:     label(i):=arg $\min_{j=1:L}$ [dist ($PR^j$, $C^i$)]
10:   end for
11:   computation of the Karcher mean for each partition PR
12:   for j:=1 to L;
13:     kj=[label(1:k):=j]; $PR^j:=M_R$ ($C^{kj}$)
14:   end for
15: end while
16: return PR Here, and according to a particular aspect of the invention, the distance dist between the matrices used here is the following Riemannian distance: if $P_1, P_2$ are two matrices, then $$dist(P_1, P_2) = \left\{ \sum_{k=1}^{K} \ln^2(\lambda_k) \right\}^{1/2}$$

in which the $\lambda_k$ are the K specific values of the joint matrix $P_1^{-1} \cdot P_2$. This Riemannian distance verifies the three properties of a distance (symmetry, separation and triangular inequality).

The computation of the Karcher mean $M_R$ of a set of matrices can be performed using a gradient descent procedure which converges rapidly (Pennec et al., 2006):

1: procedure
    C is a table of M covariance matrices.
2: CM:=C(1); d=0;
3: the mean is initialized with the first value from the table.
4: e:=$10^{-8}$;
5: while d>e
6:   W:=0;
7:   for i=1 to M
8:     W:=W+$\log_{CM}$ (C (i));

9: the tangent vectors in the tangent space are summed
10: end for
11: W:=W/M;
12: return to the variety with the exponential map and reiterate
13: CM_new:=$\exp_{CM}$(W): distance between two successive iterations
14: d=dist (CM_new, CM)
15: CM=CM_new
16: end while
17: $M_R$=CM
18: return $M_R$;
With, as operators
$\exp_{CM}$(W)=$CM^{1/2}$ exp ($CM^{-1/2}$ W $CM^{-1/2}$) $CM^{1/2}$
$\log_{CM}$(C)=$CM^{1/2}$ log ($CM^{-1/2}$ C $CM^{-1/2}$) $CM^{1/2}$ Once the reference matrices or prototypes $PR_{q,r}$ have been determined, the monitoring device computes a threshold S by the following method. The distances between each reference spatial covariance matrix $C_{m,q}^{ref}$ and the closest prototype $PR_{q,r}$ are computed, and the median distance DM of all the duly computed distances is determined. The threshold S is then taken to be equal to the arithmetic mean of the absolute values MVA of the deviations of each of the duly computed distances from the median distance DM:
1: threshold computation procedure
  C is a table of M covariance matrices.
  L is the number of prototypes
2: for i:=1 to M
3: d(i):=arg $\min_{j=1..L}$ [dist ($S^j$, $C^i$)]);
4: end for
5: MVA:=arithmetic mean (absolute value (median dist (dist)))
6: S:=MVA+$\sqrt{4\log(\text{nombrevoieEEG})}$×MVA
Key=number of EEG pathways
7: return S As a variant, the threshold can be determined in any other way. For example, the statistical mean of all the duly computed distances can be retained as threshold, increased by three standard deviations.

The preliminary step of characterization of the reference physiological state now having been carried out, the monitoring device 6 can implement the monitoring of the physiological state of the patient in real time as follows.

As indicated in FIG. 2, the monitoring device 6 measures electro-encephalographic signals of the patient in real time and thus performs measurements in M time segments are thus performed.

Each measurement gives rise to a matrix $X_m$ of n signals measured at p instants during the time segment m. Then, the monitoring device 6 filters and centers each measurement matrix $X_m$ in Q frequency bands (preferably the five usual frequency bands 1-4 Hz, 4-8 Hz, 8-12 Hz, 12-24 Hz and 24-48 Hz) to obtain M×Q filtered measurement matrices $X_{m,q}$.

From the filtered measurement matrices, M×Q standardized matrices of spatial covariance $C_{m,q}$ are determined by the formula $C_{m,q} = (X_{m,q} X_{m,q}^T)/\text{trace}(X_{m,q} X_{m,q}^T)$.

For each time segment m, the monitoring device computes a deviation from the reference physiological state $e_m$ by:

$$e_= = \sum_{q=1}^{Q} \arg\left\{\min_{r=1..R} dist(C_{m,q}, PR_{q,r})\right\}.$$

If one of the duly determined deviations is greater than the threshold S, this is then the sign that the physiological state of the patient is far from the reference physiological state.

In this case, the monitoring device 6 modifies the setpoint sent to the breathing assistance device 4 to modify its operation in a direction tending to return the patient to the reference physiological state.

The steps of FIG. 2 are repeated in a loop to enable the patient to be monitored permanently.

The p time samples of the n signals forming the measurement matrices $X_m$ or $X_m^{ref}$ can be obtained by using n distinct electro-encephalographic pathways, which makes it possible to take into account the spatial extension of the encephalographic activity. However, it is possible to reconstruct n usable signals from a smaller number r of electro-encephalographic pathways by the time plunge technique (see Lachaux et al., 1997). For this, it is sufficient to determine, for each electro-encephalographic pathway, a time delay $\Delta T$ which is preferably taken to be equal to the time delay taken by the return to the value 1/e of the self-correlation function of the electro-encephalographic pathway concerned. From a given electro-encephalographic pathway V, it is thus possible to reconstruct q virtual pathways, giving as many usable signals:

$V(t1), V(t1+\Delta T) \ldots , V(t1+k\Delta T)$ $V(t2), V(t2+\Delta T) \ldots , V(t2+k\Delta T)$

...

$V(tq), V(tq+\Delta T) \ldots , V(tq+k\Delta T)$

The parameter k is called time plunge. At the extreme, it is possible to use only a single electro-encephalographic pathway to reconstruct n virtual pathways giving the usable signals in the context of the invention. It is also possible to mix the two methods to obtain a space-time plunge, by using r electro-encephalographic pathways from each of which q virtual pathways are reconstructed such that r×q=n.

Figure 4:
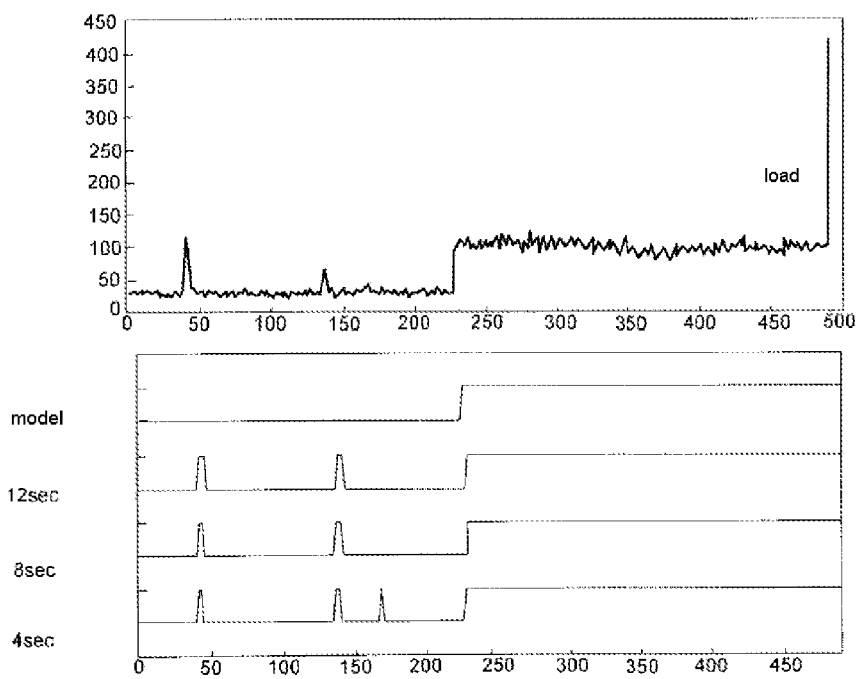
FIG. 4 is a graph illustrating the implementation of the method of the invention and the detection of a deviant physiological state.

The graph of FIG. 4 show a test of identification, according to the method of the invention, of the physiological state of a patient induced by encephalographic modifications following a respiratory stress.

The part of the curve referenced VS corresponds to a spontaneous ventilation situation used as reference, whereas the part of the curve entitled load corresponds to a provoked discord. The top graph is the deviation between the reference state and the current physiological state of the patient, plotted as a function of time.

The bottom graph is the result of the detection of the discord state, for different periods of integration over moving windows of 4, 8, 12 seconds, respectively. It is found that a few false alarms are detected in spontaneous ventilation situation over 500 windows analyzed (0.6%) following the integration performed over an overall duration of 2000 seconds. It is found that the situation of discord is detected positively by the implementation of the method of the invention.

The invention is not limited to what has just been described, but, on the contrary, encompasses any variant falling within the context defined by the claims.

In particular, although the monitoring device is here external to the assistance device, it can of course be incorporated therein.

REFERENCES

DAMASIO, A. R. (1990). "Synchronous activation in multiple cortical regions: a mechanism for recall." *Semin. Neurosci.*, 2: 287-297.

DIDAY E. (1971)—"Une nouvelle méthode en classification automatique et reconnaissance des formes: la méthode des nuées dynamiques", *Revue de Statistique Appliquée*, XIX (2), pp. 19-33, ("A new method in automatic classification and recognition of shapes: the dynamic swarms method", Applied statistics review, XIX (2), pp. 19-33).

FREEMAN, W. J. (1975). "Mass Action in the nervous system." *Academic Press*, New York.

Fletcher T., Conglin Lu, Stephen M. Pizer, and Sarang C. Joshi. (2004). "Principal geodesic analysis for the study of nonlinear statistics of shape." IEEE Transactions on Medical Imaging, 23(8):995, 2004.

GRAY, C. M., and W. SINGER. (1989). "Stimulus-specific neuronal oscillations in orientation columns of cat visual cortex." *Proc. Natl. Acad. Sci.* USA, 86 (5): 1698-1702.

Lachaux J.-P., Pezard L. Garnero L. Pelte C. Renault B. Varela F. J., Martinerie J. "Spatial Extension of Brain Activity Fools the Single-Channel Reconstruction of EEG Dynamics.", Human Brain Mapping 5:26-47 (1997)

LLINAS, R., U. RIBARY, et al. (1994). "Content and context in temporal thalamocortical binding." In: Buzsaki G. (ed): Temporal coding in the brain. Berlin and Heidelberg. Springer-Verlag., 251-272.

MILNER, P. M. (1974). "A model for visual shape recognition." *Psychol Rev.*, 81: 521-535.

MOAKHER M. (2005) "A differential geometric approach to the geometric mean of symmetric Positive-Definite matrices". *SIAM J. Matrix Anal. Appl.*, 26: 735-747.

PENNEC X., FILLARD P., and AYACHE N. (2006) "A Riemannian Framework for Tensor Computing," Int'l J. Computer Vision, 66: 41-66

RODRIGUEZ E., GEORGE N., LACHAUX J. P., MARTINERIE J., RENAULT B. and VARELA F. (1999) Perception shadow: long distance gamma band synchronization and desynchronization on the human scalp. Nature, 397: 430-433.

RODRIGUEZ E., JERBI K., LACHAUX J P. And MARTINERIE J. (2010) Brainweb 2.0: the quest for synchrony in Ten years of Nature Reviews Neuroscience: insights from the highly cited, Nature Reviews Neuroscience, 11, pp 718-726, 201

SINGER, W. (1995). "Time as coding space in neocortical processing: a hypothesis." In: Gazzaniga MS (ed): The cognitive neurosciences. Cambridge, London: The MIT Press. 91-104.

VARELA, F. J. (1995). "Resonant cell assemblies: a new approach to cognitive function and neuronal synchrony." *Biol. Res.*, 28: 81-95.

VARELA F., LACHAUX J. P., RODRIGUEZ E. & MARTINERIE J. (2001) The Brainweb: Phase synchronization and Large-scale integration. Nature Rev Neurosci., 2: 229-239.

VON DER MARLSBURG, C. (1981). "The correlation theory of brain function." *Internal Report*, 81-2. Max-Plank-Institut für Biophysikalische Chemie.

The invention claimed is:

1. A method for providing respiratory assistance using a mechanical ventilator comprising:

detecting a physiological state of a patient deviating from a reference physiological state, in which, after having determined, in each of Q frequency bands, a reference pole $PR_q$ with $q \in [1 \ldots Q]$ representative of the reference physiological state, the following steps are repeated in a loop;

performing measurements, in M time segments, of an electro-encephalographic signal of the patient along n pathways and at p instants to generate M measurement matrices $X_m$ comprising n×p samples, for $m \in [1 \ldots M]$;

filtering and centering each measurement matrix Xm in the Q frequency bands to obtain M×Q filtered measurement matrices $X_{m,q}$ and determining M×Q standardized matrices of spatial covariance by the formula $$C_{m,q} = (X_{m,q} X_{m,q}^T)/\text{trace}(X_{m,q} X_{m,q}^T);$$

for each time segment m, determining distances $d_{m,q}$ between each standardized matrix of spatial covariance $C_{m,q}$ and the reference pole $PR_q$, and determining a deviation $e_m$ from the reference physiological state as a function of the distances $d_{m,q}$;

comparing each of the deviations $e_m$ from the reference physiological state to a determined threshold S;

controlling a respiratory output of the ventilator based on each of the deviations $e_m$.

2. The method as claimed in claim 1, in which the measurement step and the computation steps are performed in real time.

3. The method as claimed in claim 1, in which each reference pole $PR_q$ is made up of R reference matrices or prototypes $PR_{q,r}$ which are determined as follows:

performing measurements, in M time segments, of an electro-encephalographic signal of the patient along n pathways and at p instants to generate M measurement matrices $X_m^{ref}$ of size n×p for $m \in [1 \ldots M]$, while the patient is in the reference physiological state;

filtering and centering each measurement matrix Xm in the Q frequency bands to obtain M×Q filtered measurement matrices $X_{m,q}^{ref}$ and determining M×Q standardized matrices of spatial covariance by the formula $$C_{m,q}^{ref} = (X_{m,q}^{ref} \cdot X_{m,q}^{ref\,T})/\text{trace}(X_{m,q}^{ref} \cdot X_{m,q}^{ref\,T});$$

determining, in each frequency band, the R reference matrices or prototypes $PR_{q,r}$ $r \in [1 \ldots R]$ from the standardized matrices of covariance $C_{m,q}^{ref}$ by using the dynamic swarms algorithm.

4. The method as claimed in claim 3, in which the threshold S is determined according to the following steps:

computing distances $d_{m,q}^{ref}$ between each covariance matrix $C_{m,q}^{ref}$ and the prototype of the prototypes $PR_{q,r}$ which is the closest thereto;

determining the median distance DM of all these computed distances $d_{m,q}^{ref}$, the threshold S being taken to be equal to the arithmetic mean of the absolute values MVA of the deviations of each of the distances $d_{m,q}$ from the median distance DM.

5. The method as claimed in claim 3, in which, for each frequency band, the distances $d_{m,q}$ between each standardized matrix of covariance and the reference pole are determined by $$d_{m,q} = \arg\left\{\min_{r=1\ldots R} dist(C_{m,q}, PR_{q,r})\right\}.$$

6. The method as claimed in claim 5, in which the deviation from the reference situation is given by the sum of the distances $$d_{m,q}: e_= = \sum_{q=1}^{Q} d_{m,q}.$$

7. The method as claimed in claim 1, in which the reference pole $PR_q$ of each frequency band is made up of the main geodesic curve defined by the covariance matrices $C_{m,q}^{ref}$ which maximizes the quantity of information.

8. The method as claimed in claim 1, in which the distances are computed in accordance with the Riemannian distance between two following matrices $P_1, P_2$:

$$dist(P_1, P_2) = \left\{ \sum_{k=1}^{K} \ln^2(\lambda_k) \right\}^{1/2}$$

in which the $\lambda_k$ are K specific values of the joint matrix $P_1^{-1} \cdot P_2$.

9. The method as claimed in claim 1, in which at least some of the pathways used for the determination of the measurement matrices are virtual pathways reconstructed from at least one electro-encephalographic pathway by the time plunge method.

10. A monitoring device for monitoring a patient to detect a physiological state deviating from a reference state of the patient, comprising:
 an electro-encephalographic signal sensor device for measuring the electro-encephalographic signals of a patient;
 a real-time signal processing computer for determining the reference poles and the threshold S, and for computing the deviations from the reference physiological state;
 a reacting device with a processor for reacting to an overshoot of the threshold S wherein the device is configure to perform a method comprising:
 detecting a physiological state of a patient deviating from a reference physiological state, in which, after having determined, in each of Q frequency bands, a reference pole $PR_q$ with $q \in [1 \ldots Q]$ representative of the reference physiological state, the following steps are repeated in a loop;
 performing measurements, in M time segments, of an electro-encephalographic signal of the patient along n pathways and at p instants to generate M measurement matrices $X_m$ comprising n×p samples, for $m \in [1 \ldots M]$;
 filtering and centering each measurement matrix Xm in the Q frequency bands to obtain M×Q filtered measurement matrices $X_{m,q}$ and determining M×Q standardized matrices of spatial covariance by the formula $$C_{m,q} = (X_{m,q} X_{m,q}^T) / \text{trace}(X_{m,q} X_{m,q}^T);$$

for each time segment m, determining distances $d_{m,q}$ between each standardized matrix of spatial covariance $C_{m,q}$ and the reference pole $PR_q$, and determining a deviation $e_m$ from the reference physiological state as a function of the distances $d_{m,q}$;
 comparing each of the deviations $e_m$ from the reference physiological state to a determined threshold S;
 controlling a respiratory output of the ventilator based on each of the deviations $e_m$.

11. The monitoring device as claimed in claim 10, in which the reaction device is configured to generate a signal warning of the threshold overshoot of the threshold S.

12. The monitoring device as claimed in claim 10, in which the processor of the reacting device further comprises a setpoint generator intended for a medical assistance device to which the patient is connected, the setpoint generator being adapted to vary a setpoint in response to the overshoot of the threshold S to modify the operation of the medical assistance device in such a way as to return the patient to the reference physiological state.

13. A device used for assisting patients in need of ventilation, wherein the medical assistance device is a breathing assistance device which comprises a monitoring device as claimed in claim 10.

14. The method as claimed in claim 1, in which the reference pole $PR_q$ of each frequency band is made up of the main geodesic curve defined by the covariance matrices $C_{m,q}^{ref}$ which maximizes the quantity of information, to at least 95%.

15. The monitoring device as claimed in claim 10, in which the reaction device comprises a speaker that generates a signal warning of the threshold overshoot.

16. A computer system for detecting a physiological state of a patient deviating from a reference physiological state, in which, after having determined, in each of Q frequency bands, a reference pole $PR_q$ with $q \in [1 \ldots Q]$ representative of the reference physiological state, the computer system executes the following steps repeatedly in a loop:
 performing measurements, in M time segments, of an electro-encephalographic signal of the patient along n pathways and at p instants to generate M measurement matrices $X_m$ comprising n×p samples, for $m \in [1 \ldots M]$;
 filtering and centering each measurement matrix Xm in the Q frequency bands to obtain M×Q filtered measurement matrices $X_{m,q}$ and determining M×Q standardized matrices of spatial covariance by the formula $$C_{m,q} = (X_{m,q} X_{m,q}^T) / \text{trace}(X_{m,q} X_{m,q}^T);$$

for each time segment m, determining distances $d_{m,q}$ between each standardized matrix of spatial covariance $C_{m,q}$ and the reference pole $PR_q$, and determining a deviation $e_m$ from the reference physiological state as a function of the distances $d_{m,q}$;
 comparing each of the deviations $e_m$ from the reference physiological state to a determined threshold S.

17. A method for detecting a physiological state of a patient deviating from a reference physiological state, in which, after having determined, in each of Q frequency bands, a reference pole $PR_q$ with $q \in [1 \ldots Q]$ representative of the reference physiological state, the following steps are repeated in a loop:
 performing measurements, in M time segments, of an electro-encephalographic signal of the patient along n pathways and at p instants to generate M measurement matrices $X_m$ comprising n×p samples, for $m \in [1 \ldots M]$;
 filtering and centering each measurement matrix Xm in the Q frequency bands to obtain M×Q filtered measurement matrices $X_{m,q}$ and determining M×Q standardized matrices of spatial covariance by the formula $$C_{m,q} = (X_{m,q} X_{m,q}^T) / \text{trace}(X_{m,q} X_{m,q}^T);$$

for each time segment m, determining distances $d_{m,q}$ between each standardized matrix of spatial covariance $C_{m,q}$ and the reference pole $PR_q$, and determining a deviation $e_m$ from the reference physiological state as a function of the distances $d_{m,q}$;
 comparing each of the deviations $e_m$ from the reference physiological state to a determined threshold S, wherein each reference pole $PR_q$ is made up of R reference matrices or prototypes $PR_{q,r}$ which are determined as follows:
  performing measurements, in M time segments, of an electro-encephalographic signal of the patient along n pathways and at p instants to generate M measurement matrices $X_m^{ref}$ of size n×p for m∈[1 . . . M], while the patient is in the reference physiological state;
  filtering and centering each measurement matrix Xm in the Q frequency bands to obtain M×Q filtered measurement matrices $X_{m,q}^{ref}$ and determining M×Q standardized matrices of spatial covariance by the formula $$C_{m,q}^{ref}=(X_{m,q}^{ref} \cdot X_{m,q}^{ref\,T})/\text{trace}(X_{m,q}^{ref} \cdot X_{m,q}^{ref\,T});$$

determining, in each frequency band, the R reference matrices or prototypes $PR_{q,r}$, r∈[1 . . . R] from the standardized matrices of covariance $C_{m,q}^{ref}$ by using the dynamic swarms algorithm,
wherein for each frequency band, the distances $d_{m,q}$ between each standardized matrix of covariance and the reference pole are determined by $$d_{m,q} = \arg\left\{\min_{r=1..R} \; dist(C_{m,q}, PR_{q,r})\right\};$$

and wherein the deviation from the reference situation is given by the sum of the $$d_{m,q} : e_= \sum_{q=1}^{Q} d_{m,q}.$$

18. A method for detecting a physiological state of a patient deviating from a reference physiological state, in which, after having determined, in each of Q frequency bands, a reference pole $PR_q$ with q∈[1 . . . Q] representative of the reference physiological state, the following steps are repeated in a loop:
  performing measurements, in M time segments, of an electro-encephalographic signal of the patient along n pathways and at p instants to generate M measurement matrices $X_m$ comprising n×p samples, for m∈[1 . . . M];
  filtering and centering each measurement matrix Xm in the Q frequency bands to obtain M×Q filtered measurement matrices $X_{m,q}$ and determining M×Q standardized matrices of spatial covariance by the formula $$C_{m,q}=(X_{m,q} X_{m,q}^T)/\text{trace}(X_{m,q} X_{m,q}^T);$$

for each time segment m, determining distances $d_{m,q}$ between each standardized matrix of spatial covariance $C_{m,q}$ and the reference pole $PR_q$, and determining a deviation $e_m$ from the reference physiological state as a function of the distances $d_{m,q}$;
  comparing each of the deviations $e_m$ from the reference physiological state to a determined threshold S,
wherein each reference pole $PR_q$ is made up of R reference matrices or prototypes $PR_{q,r}$ which are determined as follows:
  performing measurements, in M time segments, of an electro-encephalographic signal of the patient along n pathways and at p instants to generate M measurement matrices $X_m^{ref}$ of size n×p for m∈[1 . . . M], while the patient is in the reference physiological state;
  filtering and centering each measurement matrix Xm in the Q frequency bands to obtain M×Q filtered measurement matrices $X_{m,q}^{ref}$ and determining M×Q standardized matrices of spatial covariance by the formula $$C_{m,q}^{ref}=(X_{m,q}^{ref} \cdot X_{m,q}^{ref\,T})/\text{trace}(X_{m,q}^{ref} \cdot X_{m,q}^{ref\,T});$$

determining, in each frequency band, the R reference matrices or prototypes $PR_{q,r}$, r∈[1 . . . R] from the standardized matrices of covariance $C_{m,q}^{ref}$ by using the dynamic swarms algorithm,
wherein the distances are computed in accordance with the Riemannian distance between two following matrices $P_1, P_2$:

$$dist(P_1, P_2) = \left\{\sum_{k=1}^{K} \ln^2(\lambda_k)\right\}^{1/2}$$

in which the $\lambda_k$ are K specific values of the joint matrix $P_1^{-1} \cdot P_2$.

19. A method for providing respiratory assistance using a mechanical ventilator comprising:
  detecting a physiological state of a patient deviating from a reference physiological state, in which, after having determined, in each of Q frequency bands, a reference pole $PR_q$ with q∈[1 . . . Q] representative of the reference physiological state, the following steps are repeated in a loop;
  performing measurements, in M time segments, of an electro-encephalographic signal of the patient along n pathways and at p instants to generate M measurement matrices $X_m$ comprising n×p samples, for m∈[1 . . . M];
  filtering and centering each measurement matrix Xm in the Q frequency bands to obtain M×Q filtered measurement matrices $X_{m,q}$ and determining M×Q standardized matrices of spatial covariance by the formula $$C_{m,q}=(X_{m,q} X_{m,q}^T)/\text{trace}(X_{m,q} X_{m,q}^T);$$

for each time segment m, determining distances $d_{m,q}$ between each standardized matrix of spatial covariance $C_{m,q}$ and the reference pole $PR_q$, and determining a deviation $e_m$ from the reference physiological state as a function of the distances $d_{m,q}$;
  comparing each of the deviations $e_m$ from the reference physiological state to a determined threshold S;
  controlling a respiratory output of the ventilator based on each of the deviation $e_m$
wherein each reference pole $PR_q$ is made up of R reference matrices or prototypes $PR_{q,r}$ which are determined as follows:
  performing measurements, in M time segments, of an electro-encephalographic signal of the patient along n pathways and at p instants to generate M measurement matrices $X_m^{ref}$ of size n×p for m∈[1 . . . M], while the patient is in the reference physiological state;
  filtering and centering each measurement matrix Xm in the Q frequency bands to obtain M×Q filtered measurement matrices $X_{m,q}^{ref}$ and determining M×Q standardized matrices of spatial covariance by the formula $$C_{m,q}^{ref}=(X_{m,q}^{ref} \cdot X_{m,q}^{ref\,T})/\text{trace}(X_{m,q}^{ref} \cdot X_{m,q}^{ref\,T});$$

determining, in each frequency band, the R reference matrices or prototypes $PR_{q,r}$, r∈[1 . . . R] from the standardized matrices of covariance $C_{m,q}^{ref}$ by using the dynamic swarms algorithm,
wherein for each frequency band, the distances $d_{m,q}$ between each standardized matrix of covariance and the reference pole are determined by $$d_{m,q} = \arg\left\{\min_{r=1..R} dist(C_{m,q}, PR_{q,r})\right\};$$

and wherein the deviation from the reference situation is given by the sum of the distances $$d_{m,q} : e_= = \sum_{q=1}^{Q} d_{m,q},$$

and wherein the distances are computed in accordance with the Riemannian distance between two following matrices $P_1, P_2$:

$$dist(P_1, P_2) = \left\{\sum_{k=1}^{K} \ln^2(\lambda_k)\right\}^{1/2}$$

in which the $\lambda_k$ are K specific values of the joint matrix $P_1^{-1} \cdot P_2$.

20. A monitoring device for monitoring a patient to detect a physiological state deviating from a reference state of the patient, comprising:
an electro-encephalographic signal sensor device (5) for measuring the electro-encephalographic signals of a patient;
a real-time signal processing computer (7) for determining the reference poles $PR_q$ and the threshold S, and for computing the deviations $e_m$ from the reference physiological state;
a reacting device (8) for reacting to an overshoot of the threshold S wherein the device is configure to perform a method comprising:
detecting a physiological state of a patient deviating from a reference physiological state, in which, after having determined, in each of Q frequency bands, a reference pole $PR_q$ with $q \in [1 \ldots Q]$ representative of the reference physiological state, the following steps are repeated in a loop;
performing measurements, in M time segments, of an electro-encephalographic signal of the patient along n pathways and at p instants to generate M measurement matrices $X_m$ comprising n×p samples, for $m \in [1 \ldots M]$;
filtering and centering each measurement matrix Xm in the Q frequency bands to obtain M×Q filtered measurement matrices $X_{m,q}$ and determining M×Q standardized matrices of spatial covariance by the formula $$C_{m,q} = (X_{m,q} X_{m,q}^T)/\text{trace}(X_{m,q} X_{m,q}^T);$$

for each time segment m, determining distances $d_{m,q}$ between each standardized matrix of spatial covariance $C_{m,q}$ and the reference pole $PR_q$, and determining a deviation $e_m$ from the reference physiological state as a function of the distances $d_{m,q}$;
comparing each of the deviations $e_m$ from the reference physiological state to a determined threshold S;
controlling a respiratory output of the ventilator based on each of the deviation $e_m$,
wherein each reference pole $PR_q$ is made up of R reference matrices or prototypes $PR_{q,r}$ which are determined as follows:
performing measurements, in M time segments, of an electro-encephalographic signal of the patient along n pathways and at p instants to generate M measurement matrices $X_m^{ref}$ of size n×p for $m \in [1 \ldots M]$, while the patient is in the reference physiological state;
filtering and centering each measurement matrix Xm in the Q frequency bands to obtain M×Q filtered measurement matrices $X_{m,q}^{ref}$ and determining M×Q standardized matrices of spatial covariance by the formula $$C_{m,q}^{ref} = (X_{m,q}^{ref} \cdot X_{m,q}^{ref\,T})/\text{trace}(X_{m,q}^{ref} \cdot X_{m,q}^{ref\,T});$$

determining, in each frequency band, the R reference matrices or prototypes $PR_{q,r}$ $r \in [1 \ldots R]$ from the standardized matrices of covariance $C_{m,q}^{ref}$ by using the dynamic swarms algorithm,
wherein for each frequency band, the distances $d_{m,q}$ between each standardized matrix of covariance and the reference pole are determined by $$d_{m,q} = \arg\left\{\min_{r=1..R} dist(C_{m,q}, PR_{q,r})\right\};$$

and wherein the deviation from the reference situation is given by the sum of the distances $$d_{m,q} : e_= = \sum_{q=1}^{Q} d_{m,q},$$

and wherein the distances are computed in accordance with the Riemannian distance between two following matrices $P_1, P_2$:

$$dist(P_1, P_2) = \left\{\sum_{k=1}^{K} \ln^2(\lambda_k)\right\}^{1/2}$$

in which the $\lambda_k$ are K specific values of the joint matrix $P_1^{-1} \cdot P_2$.

* * * * *